(12) United States Patent
Chang et al.

(10) Patent No.: US 10,383,829 B2
(45) Date of Patent: Aug. 20, 2019

(54) PROCESS FOR FORMING JANUS PARTICLES AND APPLICATION THEREOF

(71) Applicant: National Taiwan University, Taipei (TW)

(72) Inventors: Huan-Tsung Chang, Taipei (TW); Tzu-Heng Chen, Taipei (TW); Arun Prakash Periasamy, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 15/948,233

(22) Filed: Apr. 9, 2018

(65) Prior Publication Data
US 2018/0221291 A1    Aug. 9, 2018

Related U.S. Application Data

(62) Division of application No. 15/440,353, filed on Feb. 23, 2017, now Pat. No. 9,962,337.

(60) Provisional application No. 62/349,128, filed on Jun. 13, 2016.

(51) Int. Cl.
*A61K 9/51* (2006.01)
*A61K 9/06* (2006.01)

(52) U.S. Cl.
CPC .................. *A61K 9/51* (2013.01); *A61K 9/06* (2013.01); *A61K 9/5123* (2013.01)

(58) Field of Classification Search
CPC ....................................................... A61K 9/51
See application file for complete search history.

(56) References Cited

U.S. PATENT DOCUMENTS 7,875,654 B2    1/2011  Hong et al.
9,831,010 B2   11/2017  Bayley et al.

FOREIGN PATENT DOCUMENTS

WO    WO-2016084849 A1 *  6/2016  ............. A61K 47/14

* cited by examiner

*Primary Examiner* — Kyle A Purdy
(74) *Attorney, Agent, or Firm* — WPAT, PC

(57) ABSTRACT

The present invention provides a process for forming Janus particles. The novel application of the Janus particles is also disclosed in the present invention. In particular, the Janus particles have an average diameter less than 10 nm and a peak between 2850 and 2921 $cm^{-1}$ in Fourier transform infrared spectrum.

7 Claims, 25 Drawing Sheets

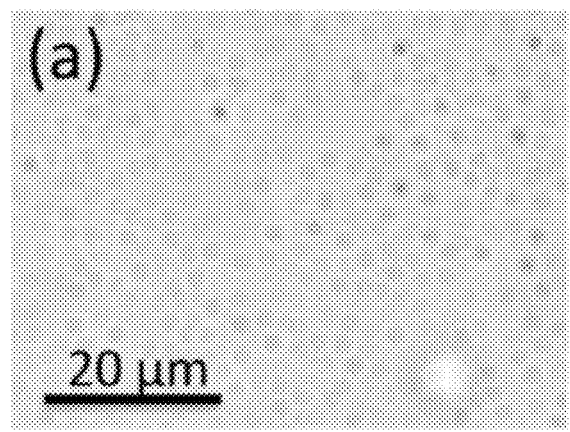
Figure 2(C)-(a)

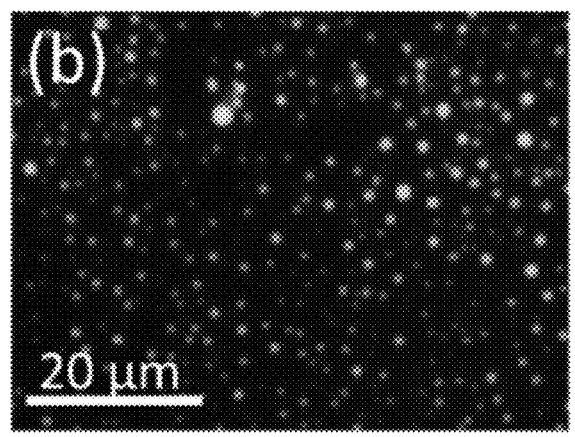
Figure 2(C)-(b)

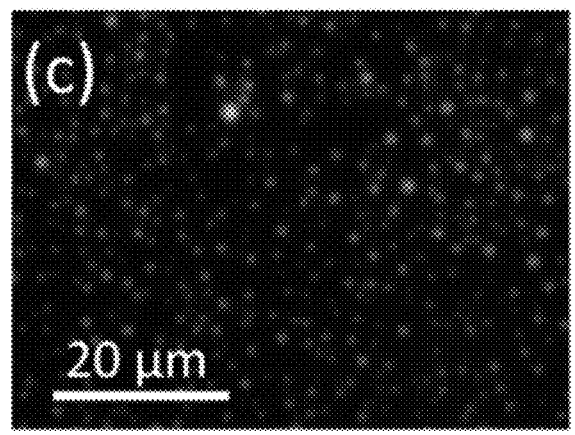
Figure 2(C)-(c)

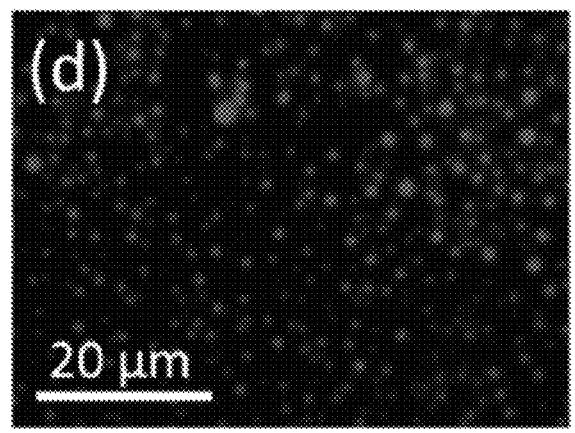
Figure 2(C)-(d)

PROCESS FOR FORMING JANUS PARTICLES AND APPLICATION THEREOF

CROSS-REFERENCE TO RELATED APPLICATIONS

This is a divisional of U.S. Ser. No. 15/440,353, filed on Feb. 23, 2017 by the same inventors, and claims priority there from. This divisional application contains rewritten claims to the restricted-out subject matter of original claims

TECHNICAL FIELD OF THE INVENTION

The present invention relates to a process for forming a substance with a superstructure and Janus particles. The novel application of the substance with the superstructure and the Janus particles are also provided in the present invention. The substance with the superstructure comprises vesicle and hydrogel. The vesicle and hydrogel are prepared in a solution with different ionic strength range.

BACKGROUND OF THE INVENTION

Highly ordered superstructures of molecules or (nano) particles have attracted great attention because they possess both characters of monomers and their collective properties. Molecular components through various noncovalent interactions such as multiple hydrogen bonding, metal coordination, and aromatic stacking have been used for preparation of supramolecular polymers that have self-healing properties (sensitive response to stimuli) and self-repairing capacity.

Xu et al. (*Chem. Soc. Rev.* 2013, 42 (7), 3114-3126.) disclosed one (1-D), two (2-D), and three-dimensional (3-D) superstructures with various morphologies such as wires, spirals, column, and sheets have been prepared through self-assembly.

Wang et al. (*ACS Nano* 2010, 4 (3), 1587-1595) further taught these self-assembled superstructures can retain the properties of individual nanoparticles and have shown promising in various applications such as optical and electronic sensors, biomedicals, and energy related materials in batteries.

However, preparation of high-quality and large-scale self-assembled superstructures is an very difficult task. It requires particular attention in controlling many experimental factors such as the surface ligand, core, and solvent, mainly because they affect the interactions between/among nanoparticles through various forces such as van der Waals, electrostatic, and entropic particle-particle interactions.

Based on the aforementioned, the important target of current industries is to develop a process for large scale self-assembly of supermolecule that can form new materials with both characters of monomers and collective properties and a new family of self-assembly material made from a fabricates from easy-obtain, non-expensive precursor and gree process consisted with polymer-like properties.

SUMMARY OF THE INVENTION

In one aspect, the present invention disclosed a process for forming a substance with a superstructure, said process comprises following steps:

Provide carbon dots that have an average diameter less than 10 nm; Form a elastomer through self-assembly of the carbon dots below 250° C.; Perform a reaction to have the elastomer form Janus particles, and treat the Janus particles with a solution to form the substance with the superstructure. The substance with the superstructure comprises vesicle and hydrogel.

The feature of the invention process is to prepare various substances with the superstructures only through simple control of the ionic strength of the solution. In one embodiment, the vesicle is formed in the solution that has an ionic strength between 100 and 10000 mM. In another embodiment, the hydrogel is formed in the solution that has an ionic strength between 10 and 100 mM In general, the invented vesicle or hydrogel is isolated after removing the solution by filtration or dialysis process.

In another aspect, the present invention provides a vesicle. The vesicle comprises a plurality of Janus particles with an average diameter less than 10 nm, a peak between 2850 and 2921 $cm^{-1}$ in Fourier transform infrared spectrum and has a quantum yield more than 20%. The aforementioned vesicle is mainly as a carrier for delivering chemicals, such as a drug. In one example, the vesicle is a liposome.

Typically, the vesicle has an onion-like double-layered structure. Through van der Waal interactions, the Janus particles with solvophobicity properties form the vesicle. The morphology of vesicle does not undergo significant changes when the temperature is varied. When compared to traditional liposomes prepared from lipids or polymers, the vesicle is much more stable and shows excitation-wavelength dependence emission properties. Therefore, the vesicle has great potentials for biomedical applications.

In still another aspect, the present invention disclosed a process for forming Janus particles, said process comprises following steps:

Provide carbon dots that have an average diameter less than 10 nm; Form a elastomer through self-assembly of the carbon dots below 250° C.; and perform a reaction to have the elastomer form Janus particles, which have an average diameter less than 10 nm and a peak between 2850 and 2921 $cm^{-1}$ in Fourier transform infrared spectrum.

In one representative embodiment, the invention process for forming the Janus particles is to use glycerol trioleate to prepare the carbon dots and the as-prepared carbon dots are used to form the elastomer through self-assembly. Through transesterification, the elastomer is converted from hexagonally packing to cubic packing, leading to formation of the Janus particles.

Accordingly, the present invention discloses a novel and easy to scale-up process for forming the invention substance with the superstructure. Secondly, the present invention provides a novel vesicle that has potential application in biomedical area due to its unique physichemco properties. Thirdly, the process for forming Janus particles is provided in the present invention. The Janus particles are further treated with a solution to form the substance with 3-D superstructures like vesicle, liposome and hydrogel by controlling the ionic strength of the solution.

BRIEF DESCRIPTION OF THE DRAWINGS

FIG. 2(B) is HRTEM image of the vesicle and FIGS. 2(C)-(a) to 2(C)-(d) are Optical images of the vesicle, which of FIG. 2(C)-(a) is under bright field, FIG. 2(C)-(b) is under dark field excited at the wavelengths of 400 nm, FIG. 2(C)-(c) is under dark field excited at the wavelengths of 488 nm, and FIG. 2(C)-(d) is under dark field excited at the wavelengths of 532 nm;

BRIEF DESCRIPTION OF THE PREFERRED EMBODIMENTS

Figure 1A:
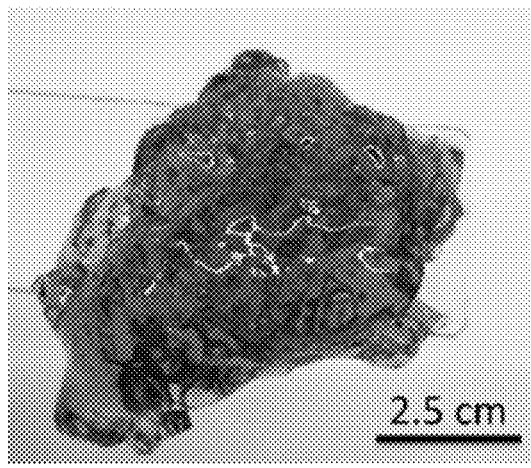
FIG. 1(A) is a photo of the invented elastomer prepared from glycerol trioleate.

In a first embodiment, the present invention disclosed a process for forming a substance with a superstructure, said process comprises following steps:

Provide carbon dots that have an average diameter less than 10 nm; Form a elastomer through self-assembly of the carbon dots below 250° C.; Perform a reaction to have the elastomer form Janus particles, and treat the Janus particles with a solution to form the substance with the superstructure. The substance with the superstructure comprises vesicle and hydrogel. The vesicle is formed in the solution that has an ionic strength between 100 and 10000 mM, and the hydrogel is formed in the solution that has an ionic strength between 10 and 100 mM.

In one example of the first embodiment, the carbon dots are synthesized from a molecule that has 8-100 carbon numbers. The molecule that has 8-100 carbon numbers further comprises carbonyl groups, amide groups, ester groups, carboxylic acid groups, hydroxyl groups, amino groups, thiol groups and ether groups.

In one preferred example of the first embodiment, the carbon dots are synthesized from glyceryl ester. Preferably, the glyceryl ester comprises monoglycerides, diglycerides, and triglycerides.

In one example of the first embodiment, the reaction comprises transesterification and hydrolysis. Preferably, the hydrolysis is carried out in the presence of a base that comprises NaOH and KOH. The transesterification is carried out in a catalyst comprises sodium methoxide and sodium ethoxide.

In one example of the first embodiment, the Janus particles have an average diameter less than 10 nm and a peak between 2850 and 2921 $cm^{-1}$ in Fourier transform infrared spectrum. Preferably, the Janus particles have an average diameter less than 2 nm.

In one example of the first embodiment, the Janus particles have hydrophobic groups on first surfaces and hydrophilic groups selected from the group consisting of carbonyl groups, amide groups, ester groups, hydroxyl groups, amino groups, thiol groups, carboxylic acid groups and the combination thereof on second surfaces opposite to the first surfaces.

In one example of the first embodiment, the vesicle has an average diameter less than 3 μm.

In one example of the first embodiment, the hydrogel is a self-healing substance.

In a second embodiment, the present invention provides a vesicle. The vesicle comprises a plurality of Janus particles with an average diameter less than 10 nm, a peak between 2850 and 2921 $cm^{-1}$ in Fourier transform infrared spectrum and has a quantum yield more than 20%. The aforementioned vesicle is mainly as a carrier for delivering chemicals.

The vesicle is formed through van der Waal interactions between each one of the Janus particle. The Janus particles have hydrophobic groups on first surfaces and hydrophilic groups that selected from the group consisting of carbonyl groups, amide groups, ester groups, hydroxyl groups, amino groups, thiol groups, carboxylic acid groups and the combination thereof on second surfaces opposite to the first surfaces.

In one example of the second embodiment, the vesicle has an average diameter less than 3 μm.

In one preferred example of the second embodiment, the vesicle comprises a plurality of the Janus particles with an average diameter less than 2 nm, a peak between 2850 and 2921 $cm^{-1}$ in Fourier transform infrared spectrum and has a quantum yield more than 50%. Preferably, the vesicle has a quantum yield more than 90%.

In one example of the second embodiment, the vesicle is a carrier for delivering one that comprises a drug.

In a third embodiment, the present invention disclosed a process for forming Janus particles, said process comprises following steps:

Provide carbon dots that have an average diameter less than 10 nm; Form a elastomer through self-assembly of the carbon dots below 250° C.; and perform a reaction to have the elastomer form Janus particles, which have an average diameter less than 10 nm and a peak between 2850 and 2921 $cm^{-1}$ in Fourier transform infrared spectrum.

In one representative example of the third embodiment, glycerol trioleate is as a raw material for preparing the carbon dots at 250° C. At this temperature, glyceryl trioleate decomposed slowly to form glycerol and oleic acid, which then led to form the carbon dots. The prepared carbon dots with an average diameter less than 10 nm form the elastomer through self-assembly at room temperature. Through transesterification under alkaline condition, the elastomer was converted from hexagonally packing to cubic packing, leading to formation of the Janus particles.

In one example of the third embodiment, the carbon dots are prepared from a molecule that has 8-100 carbon numbers. Preferably, the molecule that has 8-100 carbon numbers further comprises carbonyl groups, amide groups, ester groups, carboxylic acid groups, hydroxyl groups, amino groups, thiol groups and ether groups.

In one example of the third embodiment, the carbon dots are prepared from glyceryl ester that comprises monoglycerides, diglycerides, and triglycerides.

In one example of the third embodiment, the reaction comprises transesterification and hydrolysis. Preferably, the hydrolysis is carried out in the presence of a base that comprises NaOH and KOH. The transesterification is carried out in a catalyst comprises sodium methoxide and sodium ethoxide.

In one example of the third embodiment, the Janus particles have hydrophobic groups on first surfaces and hydrophilic groups selected from the group consisting of carbonyl groups, amide groups, ester groups, hydroxyl groups, amino groups, thiol groups, carboxylic acid groups and the combination thereof on second surfaces opposite to the first surfaces.

In one example of the third embodiment, the Janus particles are used for forming vesicles or hydrogels.

Characterization

Transmission electron microscopy (TEM) and high-resolution TEM (HRTEM) images were recorded using JSM-1200EX II (JEOL Ltd., Tokyo, Japan) and FEI Tecnai-G2-F20 instruments equipped with a Philips Technai G2 dispersive X-ray spectrometer. The fluorescence spectra were measured with a Cary Eclipse PL spectrophotometer from Varian (Mulgrave, Victoria, Australia). FT-IR spectra of samples on NaF plates were recorded using an iS 5 system from Thermo Fisher Scientific.

Preparation of Dip Coating Films

A dip coating method and Fourier filtering were applied to reconstruct an original HRTEM image to characterize the as-formed hydrophilic superstructures of the carbon dots.

The as-prepared carbon dots products were separately dispersed in ethanol solution (5%). Each of them was then separately dipped onto a water solution. Each of the films was collected using a formar coated copper grid from the air-water interface.

Viscosity Analysis

The apparent viscosity was measured on a DV1 viscosity meter from Brookfield (Middleboro, Mass., USA) equipped with a temperature controller using spindle CPA-40Z with 30 rpm. All the samples were subjected to sonication at 55° C. for 20 min. The static viscosity data were recorded in a period of 20 s. The rheological data with different shear rates were recorded after the solutions were prepared for at least 0.5 h (their viscosity reached equilibrium).

Example 1: Formation of the Elastomer Consisting of the Carbon Dots

Glyceryl trioleate as a precursor was used to form the carbon dots at 220° C. for 3 days, mainly through condensation, polymerization, carbonization, and passivation of glycerol trioleate. At this temperature, glyceryl trioleate was decomposed slowly to form glycerol and oleic acid, which then led to form the carbon dots. When the carbon dots solution was slowly cooled down, it became more viscous and eventually formed the elastomer (FIG. 1(A)) at ambient temperature (25° C.).

Figure 1B:
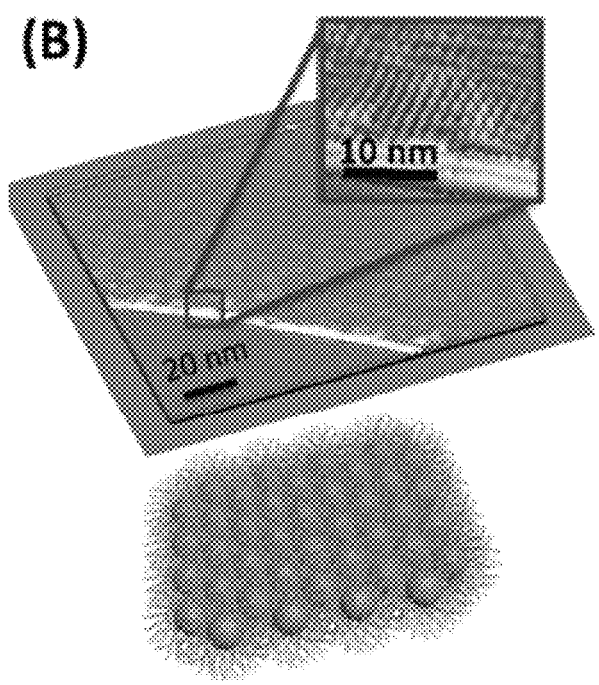
FIG. 1(B) is Reconstructed HRTEM image of the invented elastomer prepared from glycerol trioleate and FIG. 1(C) is DSC curve of the invented elastomer prepared from glycerol trioleate.
Figure 5:
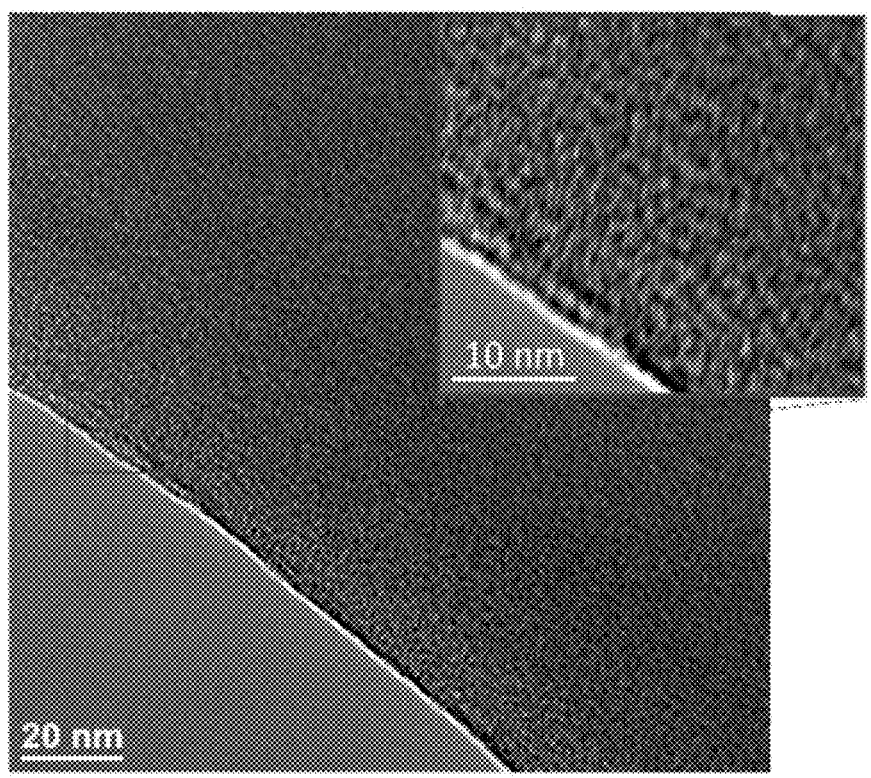
FIG. 5 is HRTEM image of the elastomer, which a thin film of the elastomer was prepared using the dip-coating method.
Figure 6:
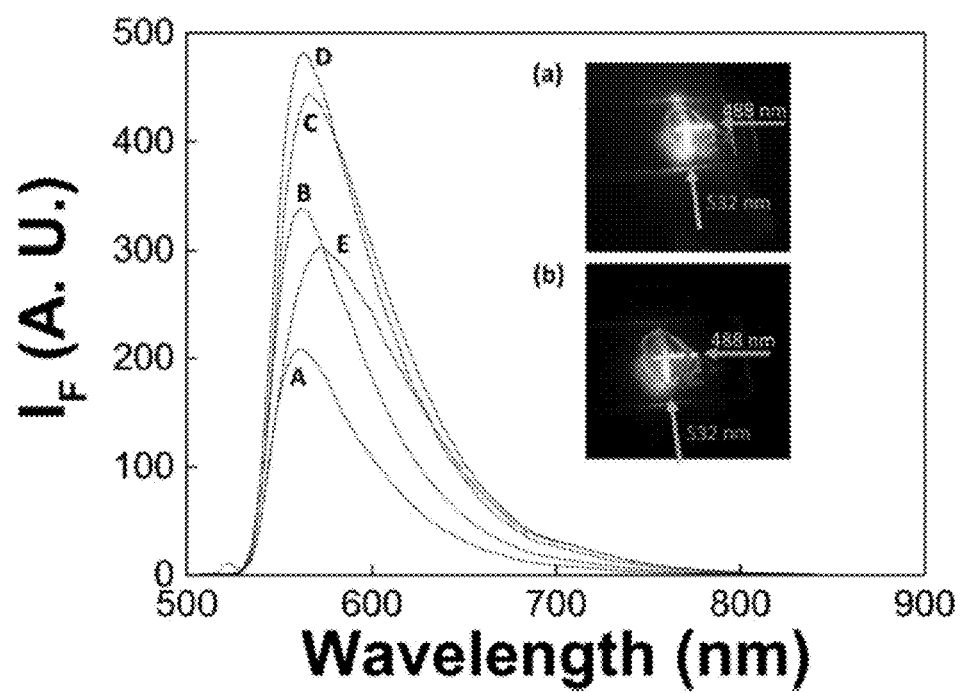
FIG. 6 is Fluorescence spectra of the elastomer, where excitation wavelength at (A) 400, (B) 430, (C) 460, (D) 490, and (E) 520 nm. Inset: photograph of the elastomer excited separately with lasers at 488 nm and 532 nm in the (a) absence (b) presence of a long-pass (540 nm) filter

The HRTEM (High Resolution Transmission Electron Microscopy) image depicted in FIG. 5 displays that the elastomer consists of the carbon dots (<1 nm) with hexagonal closest packing, revealing that the elastomer was formed through self-assembly of the carbon dots. The reasoning was supported with a reconstructed HRTEM image as shown in FIG. 1(B) that had been obtained after removing non-periodical signals from the original TEM image by applying a Fourier filtering technique. The elastomer emits strong yellow fluorescence, with negligible excitation-wavelength dependence of emission properties as shown in FIG. 6. The elastomer possesses strong elasticity and adhesiveness at ambient temperature and pressure. The elastomer lost its adhesiveness at 0° C., which recovered by increasing the temperature up to 20° C. As a result, the elastomer is a self-healing substance.

Figure 1C:
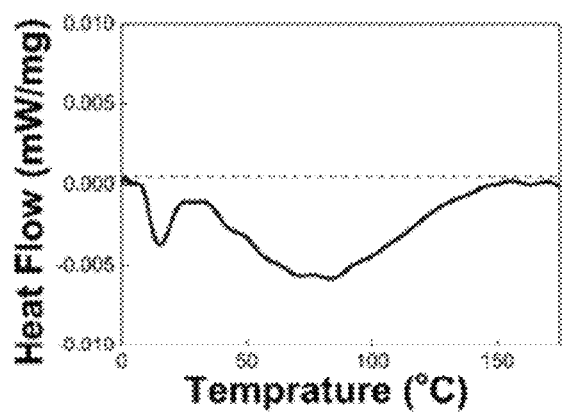

FIG. 1(C) shows the differential scanning calorimetry (DSC) curve of the elastomer, with two peaks at 15.4 and 84.8° C. that are assigned for its glass transition temperature and melting temperature, respectively. The elastomer also provides self-healing properties. At ambient temperature, the film of the elastomer was cut to two pieces and shows negligible healing properties at ambient temperature after a period of 100 h, while being self-healed completely at 100° C. after a period of 2 h. The self-healing of the elastomer is through the reconstruction of the carbon dots arrangement, mainly due to the van der Wall's forces between/among oleate groups on the surface of each the carbon dots. The result shows that the carbon dots have potential as a new member of self-healing materials.

Example 2: Formation of the Janus Particles

The elastomer obtained by Example 1 was converted easily to the Janus particles by treating the elastomer with NaOH/ethanol solution. Under the alkaline condition, some of the hydrophobic oleate groups on the surfaces of the carbon dots in the elastomer were released to the bulk solution, leading to exposure of OH groups on the surface of the hydrophilic superstructures of the carbon dots as evident with the Fourier transform infrared spectra (FT-IR) shown in FIG. 7(A), FIG. 7(B) and FIG. 7(C). The elastomer provides a weak signal at 3420 $cm^{-1}$ of the peak assigned for O—H stretching and a strong signal at 1710 $cm^{-1}$ assigned for C=O stretching, revealing the existence of ester groups on their surfaces. Upon increasing NaOH concentration, the intensity ratio of $v_{O-H}/v_{C=O}$ increased. At 0.5 M NaOH, the signal for $v_{C=O}$ becomes negligible, revealing most of the ester groups in the elastomer were converted to OH groups.

Figure 8:
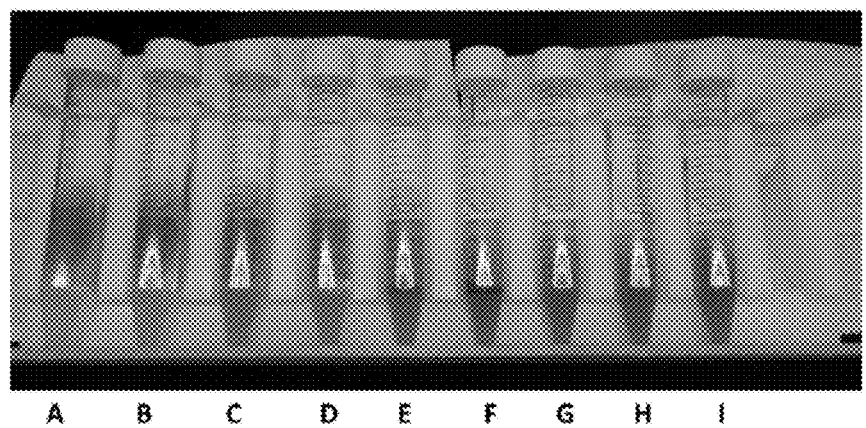
FIG. 8 is Partition of the elastomer and its products in ethyl acetate/water solutions. The elastomer was separately treated with different concentration of NaOH.

FIG. 8 shows when the solution of the elastomer was under upon increasing NaOH concentration, partition of the material in the water layer in ethyl acetate/water extracts increased, supporting the success of converting the hydrophobic elastomer to the Janus particles.

Figure 2A:
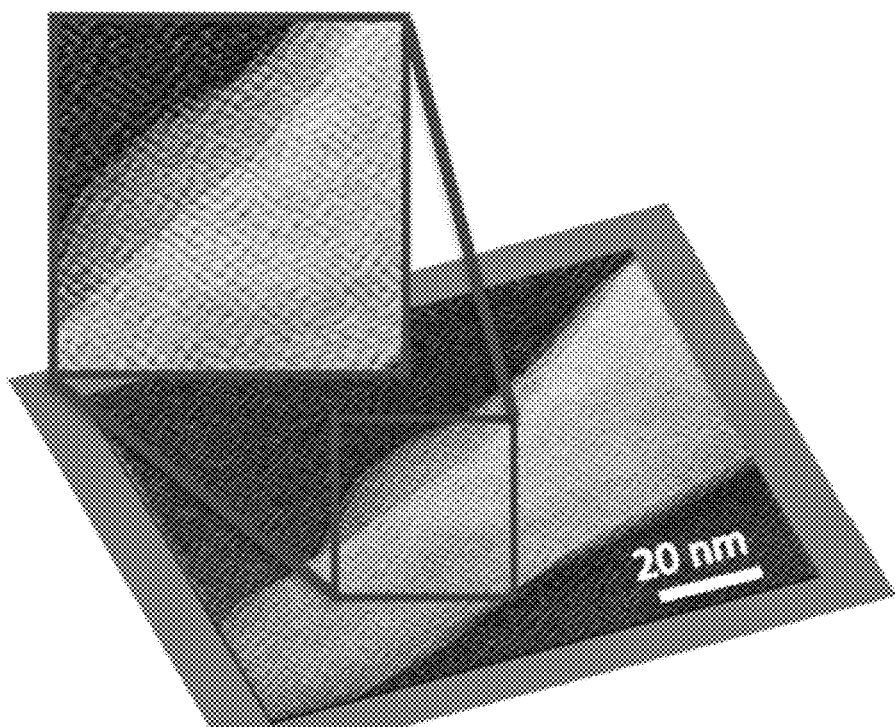
FIG. 2(A) is Reconstructed HRTEM image of the Janus particles thin film coated by dip-coating.

The reconstructed HRTEM image as shown in FIG. 2(A) reveals a 2-D super lattice structure (sheet) of the Janus particles superstructure. The hydrophilic superstructures were formed from elliptical-like the carbon dots with sizes of 0.9±0.2×1.6±0.2 nm (determine from the reconstructed HRTEM image), with a cubic-packed domain.

Figure 7A:
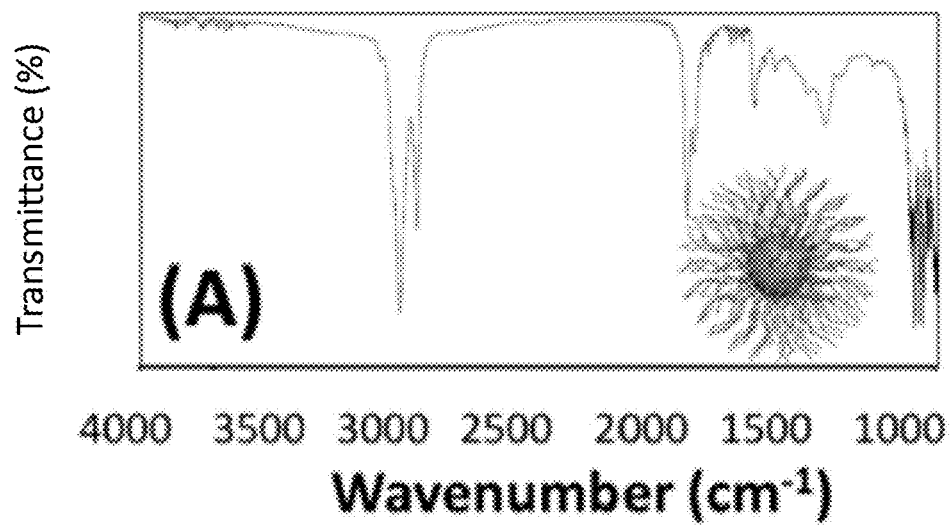
FIG. 7(A) is FT-IR spectra of the elastomer treated with 0 M NaOH/EtOH solutions.
Figure 7B:
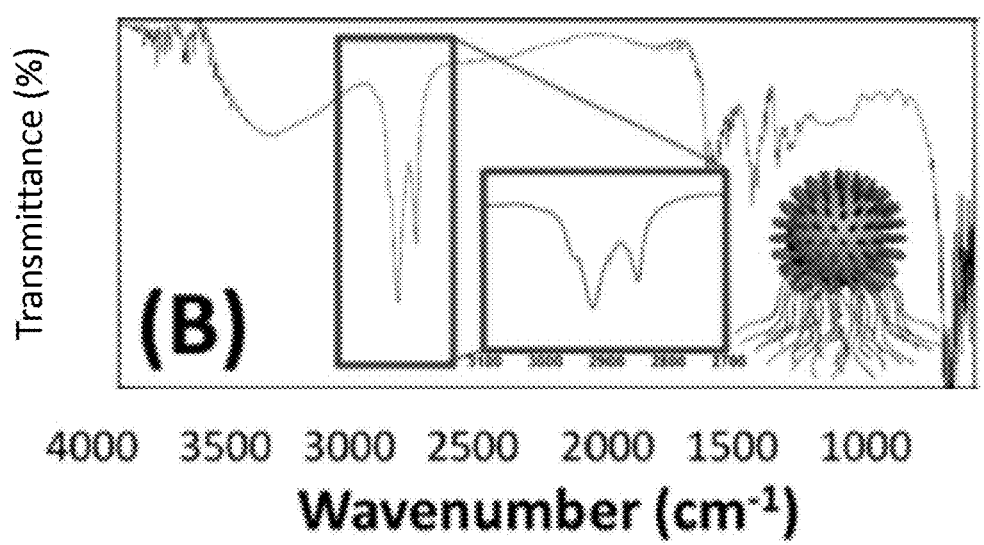
FIG. 7(B) is FT-IR spectra of the elastomer treated with 0.1 M NaOH/EtOH solutions.
Figure 7C:
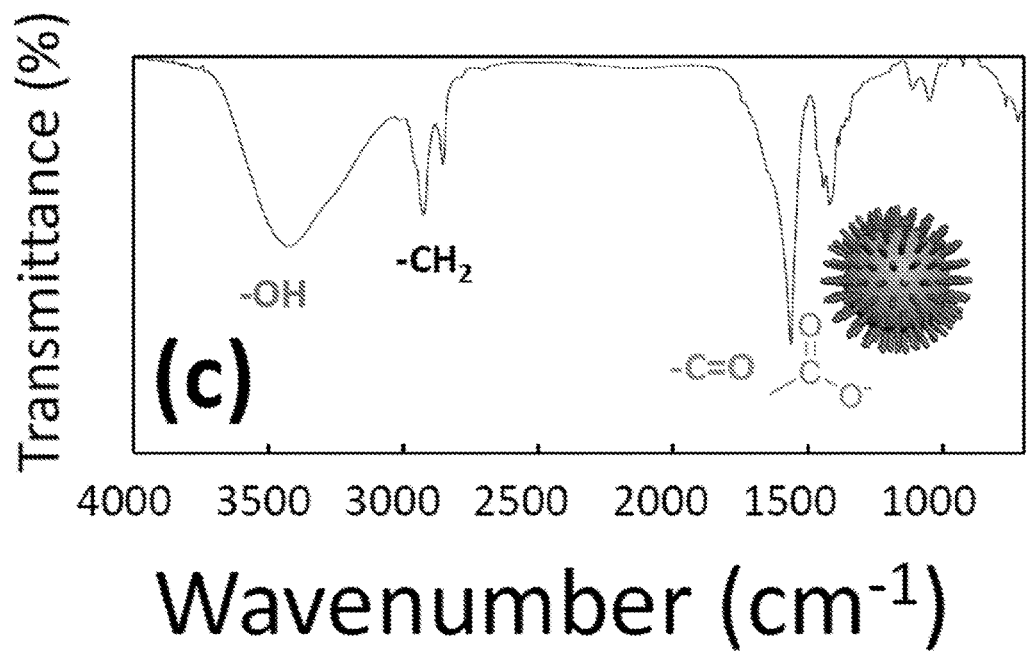
FIG. 7(C) is FT-IR spectra of the elastomer treated with 0.5 M of NaOH/EtOH.

Formation of the Janus particles superstructure is mainly due to asymmetric capping of oleate groups on the surface of the carbon dots. The symmetric and asymmetric stretching vibrations of $CH_2$ at 2920 and 2850 $cm^{-1}$ (each with a shoulder) as shown in FIG. 7(A), FIG. 7(B) and FIG. 7(C) support asymmetric capping of oleate on the surface of the carbon dots. The two intense peaks reveal that the aliphatic chains from oleate groups are packed with a high density in the long side of the carbon dots, while the two shoulder peaks reveal that the aliphatic chains on the surface of the short side were packed with less density. The cubic-packed arrangement is mainly because of the hydrogen bond interaction on the short sides that are rich in OH groups and the van der Waal forces on the long sides that are rich in aliphatic groups.

Figure 4:
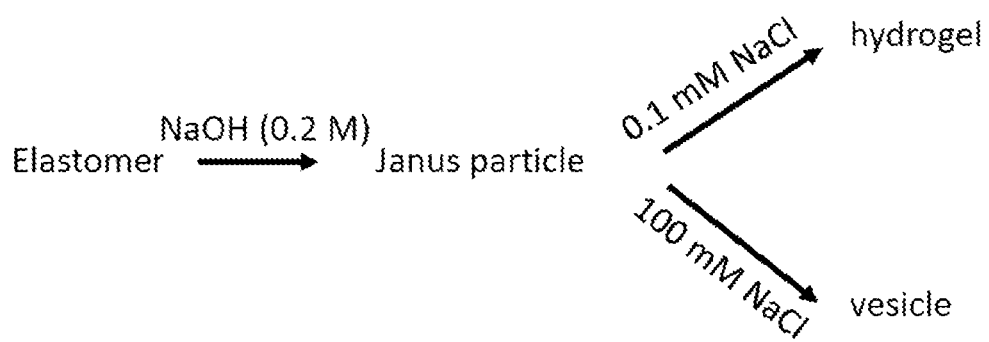
FIG. 4 is Schematic representation of the formation of Janus particles from the elastomer through esterification with 0.2 M NaOH, and formation of the hydrogels and vesicle through treatment with 100 and 0.1 mM NaCl, respectively.

FIG. 4 summarizes the conversion of the elastomer to the substance with the hydrophilic superstructure comprises vesicle and hydrogel. Initially, the oleate groups on the outmost layer of the carbon dots in the elastomer convert to form hydroxyl groups through a transesterification reaction, increasing hydrophilicity of the carbon dots on the outmost layer. Through strong hydrogen bonding between hydroxyl groups and ethanol in the bulk solution, the carbon dots in the outmost layer release from the surface of the elastomer to form a linear structure of the carbon dots. The carbon dots in the new-formed outmost layer undergoes the same reaction/releasing to form more linear structures of the carbon dots. The as-formed linear structures of the carbon dots are further broken to form the carbon dots dimers, mainly because of weak van der Waal forces between adjacent the carbon dots. Because the as-formed carbon dots dimers possess hydrophilic and hydrophobic properties on different sides, they called Janus particles. It is important to note that the Janus particles with sizes smaller than 2 nm have not been reported yet. More importantly, this simple strategy opens up a new rout for preparation of Janus particles.

Example 3: Formation of the Substance with the Superstructure

A salt out method is applied to treat the as-formed Janus particles by controlling NaCl concentration for forming the substance with the superstructure comprises vesicle and hydrogel. At 0.1 and 100 mM NaCl, hydrogels and vesicles, respectively, were prepared from the Janus particles through self-assembly as shown in FIG. 4. Unlike regular lipid molecules with a glycol or phosphate glycol as a head group, the Janus particles can be used to prepare various superstructures through simple control of the ionic strength, mainly because the Janus particles possess a much larger head group and a great number of long alkyl chains on the surface of each the carbon dots.

Figure 2B:
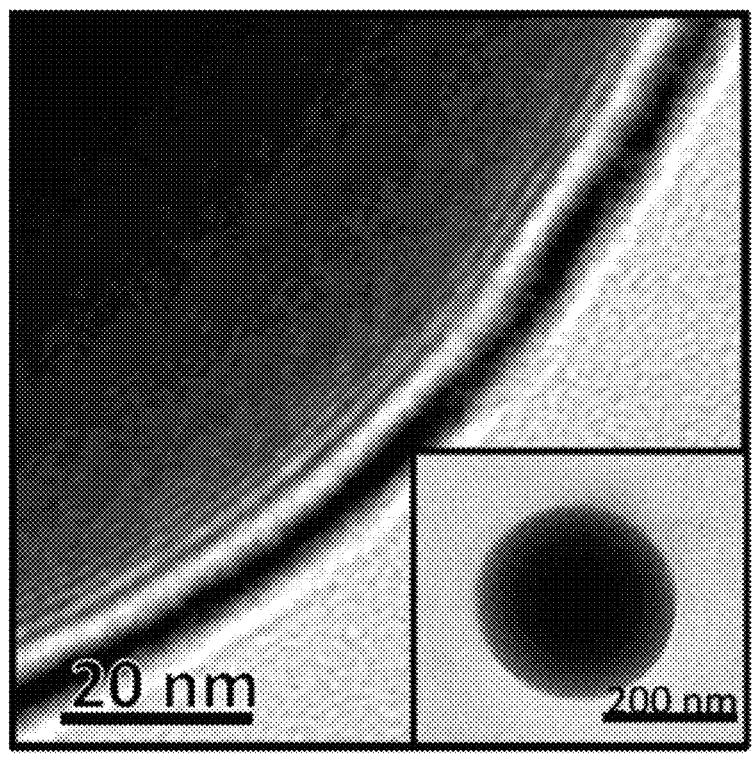
Figure 9A:
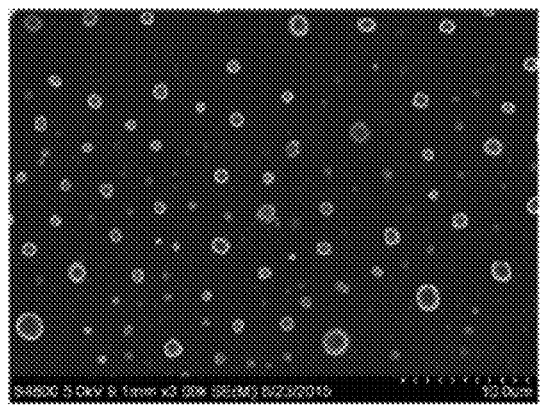
FIG. 9(A) is SEM image of the products of Janus particles after treated with (a) 100 mM NaCl solutions at 25° C. for 20 min.
Figure 9B:
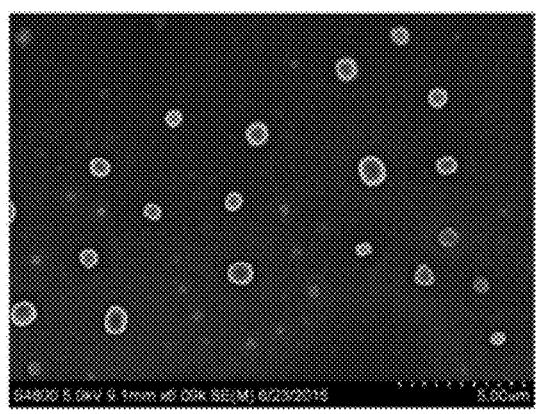
FIG. 9(B) is SEM image of the products of Janus particles after treated with (a) 50 mM NaCl solutions at 25° C. for 20 min
Figure 9C:
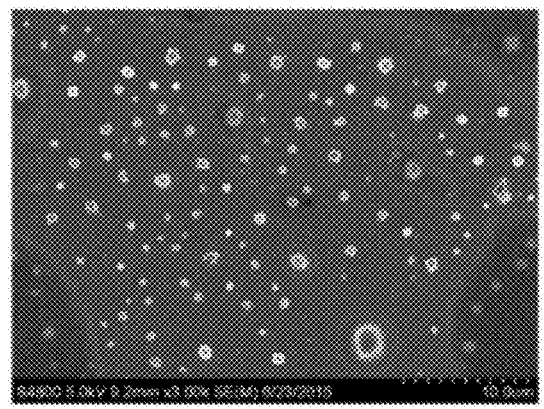
FIG. 9(C) is SEM images of the products of Janus particles after treated with (a) 10 mM of NaCl solutions at 25° C. for 20 min.

The TEM image displayed in FIG. 2(B) shows that the vesicle has an onion-like double-layered structure. Through van der Waal interactions, the Janus particles with solvophobicity properties formed the vesicles. When compared to traditional liposomes prepared from lipids or polymers, the vesicles are much more stable, and thus their structure is determined by scanning electron microscopy (SEM). The SEM images as shown in FIGS. 9(A), 9(B) and 9(C) display the salt-dependence of size and morphology of the products prepared from the Janus particles. Upon decreasing NaCl concentration from 100 to 10 mM, the size of the product decreases and the morphology changes from sphere-like to cubic-like structures. The size of the product prepared at 100 mM NaCl ranges from 0.2 to 2 μm. The bright-field optical image of the two vesicles shown in FIG. 2(C)-(a) reveal their sizes are around 2 μm, which agree with that obtained from the SEM image. The vesicle shows excitation-wavelength dependence emission properties (FIG. 2(C)-(b), FIG. 2(C)-(c) and FIG. 2(C)-(d)). The aforementioned experimental data clearly demonstrate that the invented vesicles possess fluorescence characteristics and are potentially applied in cell imaging and drug delivery. The morphology of the invented vesicles do not undergo significant changes when the temperature is varied, again showing their stable structures than liposomes prepared from conventional molecules.

Figure 3A:
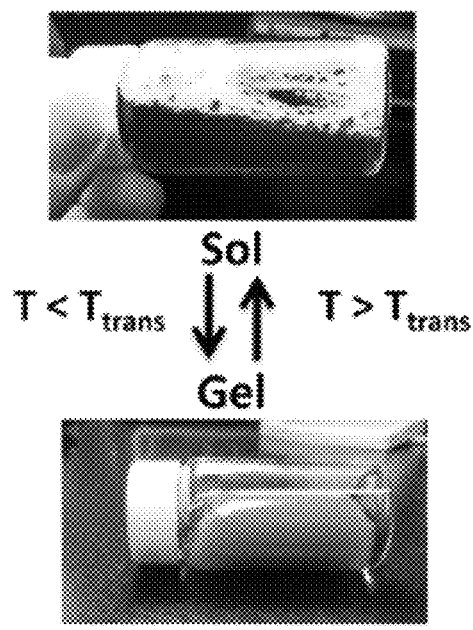
FIG. 3(A) is Photograph of the hydrogel solution at (a) 55° C. and (b) 25° C.
Figure 10:
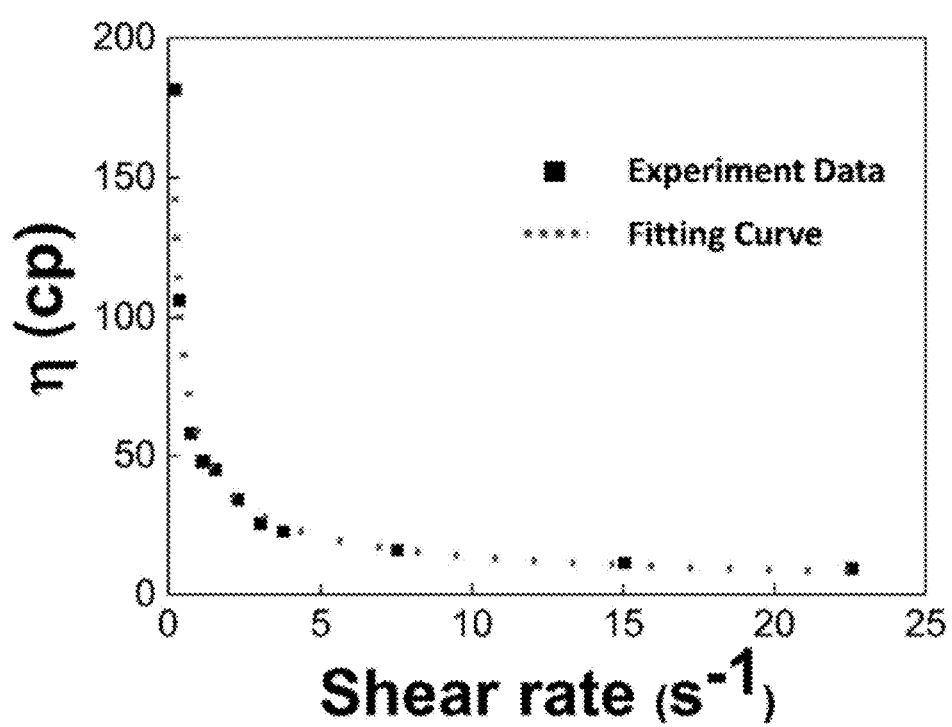
FIG. 10 is Rheogram of the hydrogel. The viscosity of the hydrogel against different shear rate from 0.2-22.5 $s^{-1}$ under 25° C.

FIG. 3(A) shows that the hydrogel was formed when the temperature was below 25° C. with 0.1 mM NaCl level. The rheogram displayed in FIG. 10 reveals that the viscosity ($\eta$) of the hydrogel solution decreased rapidly when the shear rate ($\gamma$) was increased from 0.22 to 22 $S^{-1}$, which agrees with the Power Law model (eq. 1).

$$\eta = K\gamma^{N-1} \quad \text{equation 1}$$

Figure 3B:
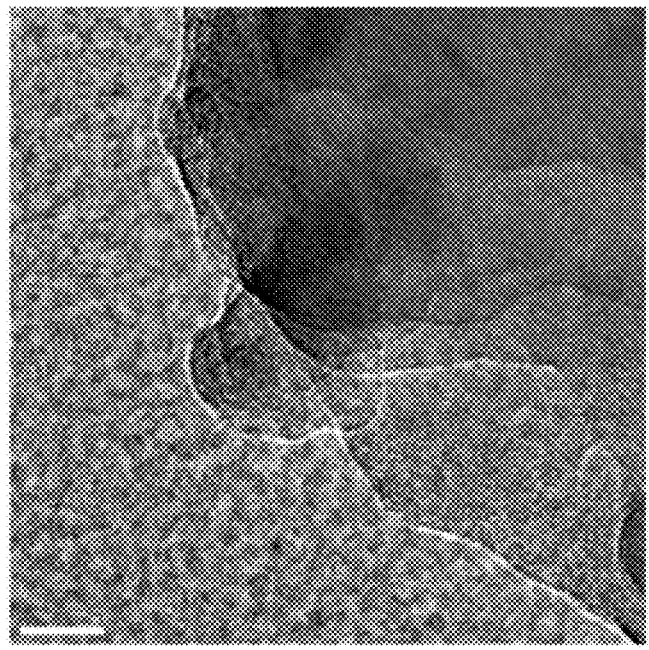
FIG. 3(B) is HRTEM image of the hydrogel.
Figure 3C:
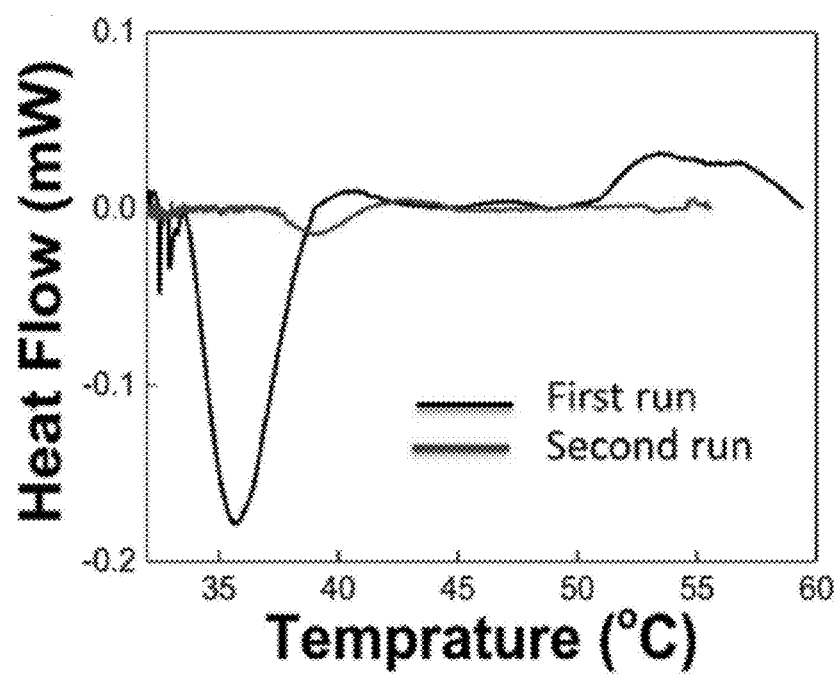
FIG. 3(C) is DSC curve of the hydrogel and FIG. 3(D) is time-dependence rheogram of the hydrogel, where Static (black square) and dynamic (red circle) conditions in (D). Inset: differential viscosity.

K is the consistency index and N is the flow behavior index. The K and N values of the hydrogel solution were determined to be 56.8 and 0.38, respectively. The thinning property of the hydrogel is similar to 5% PVA solution. This thixotropic property implies the carbon dots were self-assembled to form microstructures. The HRTEM image as shown in FIG. 3(B) shows that the hydrogel contains 2D superstructures. The DSC curve depicted in FIG. 3(C) shows a sharp peak at the temperature of 35.6° C., revealing that the superstructure of the carbon dots assembled and de-assembled below and above 35.6° C. The fast second-round measurement did not show a similar peak at the same temperature, mainly because of slow reconstruction of the hydrogel from the carbon dots solution.

Figure 11:
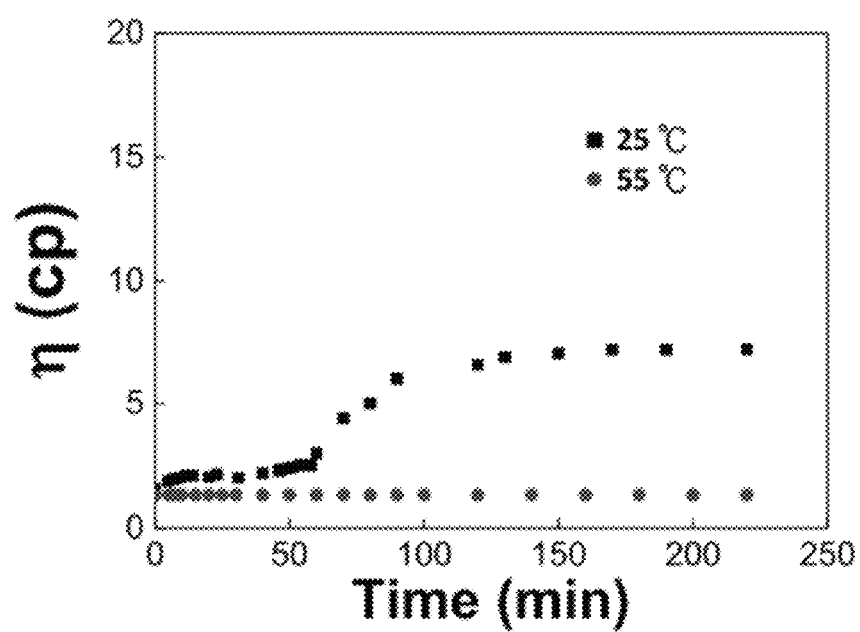
FIG. 11 is Time-dependence viscosity of the vesicle at 25° C. (black) and 55° C. (red).

Time dependent viscosity of the vesicle was measured at temperature of 55 and 25° C. and was recorded as shown in FIG. 11. When a continuous shear rate (22 $S^{-1}$) was applied to the vesicle at the temperature higher than 55° C., the viscosity did not increase with time. In contrast, the viscosity did change at temperature lower than 25° C.

Figure 3D:
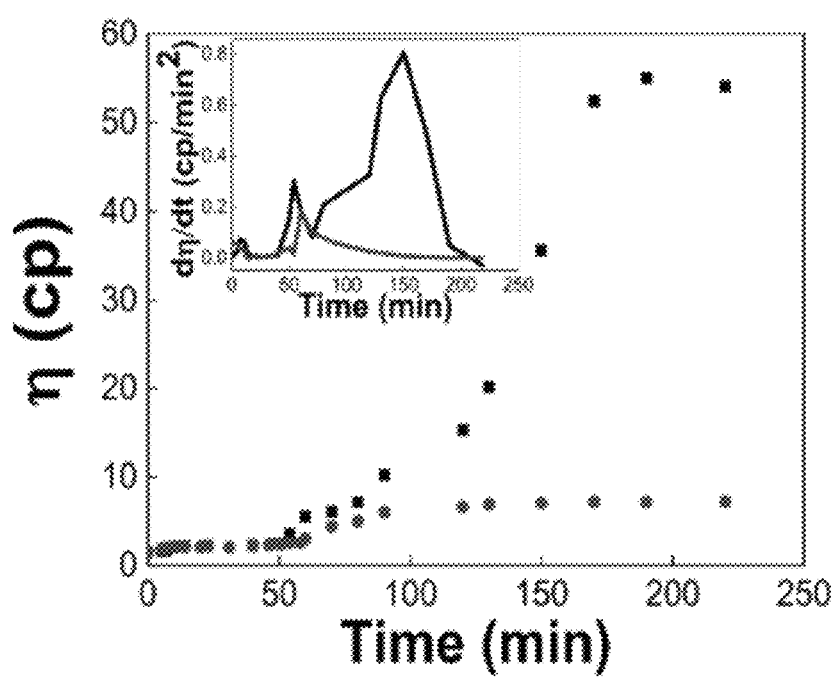

To investigate the kinetic process of the hydrogel formation, time-dependent viscosity under static and stirring conditions were recorded as shown in FIG. 3(D). The viscosity of the hydrogel solution gradually increased from 1.2 cp and reached 52 cp within 2 h at ambient temperature under a static condition. On the other hand, the viscosity only slightly increased to 7.2 cpunder continuous stirring. The differential curves (dη/dt) depicted in the inset to FIG. 3(D) shows only one sharp peak appears at 60 min under the static condition, while a small peak at 55 min and a large peak at 150 min appear under the stirring condition. The differential static and dynamic results indicate that there are two stages to form the hydrogel. The plate-shape superstructures formed through self-assembly of the carbon dots and further stacked to form long-range hydrogel structures. When the shears force was applying to the hydrogel, the long range cross-linking hydrogel structure was broken down to form small gelators, with evidence of decreased viscosity. Having such temperature and shears force dependence of viscosity properties, the hydrogel holds great potential applications in printing and drug delivery.

While the invention has explained in relation to its preferred embodiments, it is well understand that various modifications thereof will become apparent to those skilled in the art upon reading the specification. Therefore, the invention disclosed herein intended to cover such modifications as fall within the scope of the appended claims.

What is claimed is:
1. A process for forming Janus particles, said process comprising:
   (1) Providing carbon dots that have an average diameter less than 10 nm;
   (2) Forming a elastomer through self-assembly of the carbon dots below 250° C.; and

(3) Performing a reaction to have the elastomer form Janus particles, wherein the Janus particles have an average diameter less than 10 nm and a peak between 2850 and 2921 cm$^{-1}$ in Fourier transform infrared spectrum.

2. The process of claim 1, wherein the carbon dots are prepared from a molecule that has 8-100 carbon numbers.

3. The process of claim 2, wherein the molecule that has 8-100 carbon numbers further comprises carbonyl groups, amide groups, ester groups, carboxylic acid groups, hydroxyl groups, amino groups, thiol groups and ether groups.

4. The process of claim 1, wherein the carbon dots are prepared from glyceryl esters comprises monoglycerides, diglycerides, and triglycerides.

5. The process of claim 1, wherein the reaction comprises transesterification and hydrolysis.

6. The process of claim 1, wherein the Janus particles have hydrophobic groups on first surfaces and hydrophilic groups which are selected from the group consisting of carbonyl groups, amide groups, ester groups, hydroxyl groups, amino groups, thiol groups, carboxylic acid groups and the combination thereof on second surfaces opposite to the first surfaces.

7. The process of claim 1, wherein the Janus particles are used for forming vesicles or hydrogels.

\* \* \* \* \*